United States Patent
Suzuki

(10) Patent No.: US 8,858,487 B2
(45) Date of Patent: Oct. 14, 2014

(54) BLOOD PURIFICATION APPARATUS AND PRIMING METHOD THEREOF

(75) Inventor: Tomohiro Suzuki, Makinohara (JP)

(73) Assignee: Nikkiso Company Limited, Tokyo (JP)

( * ) Notice: Subject to any disclaimer, the term of this patent is extended or adjusted under 35 U.S.C. 154(b) by 0 days.

(21) Appl. No.: 13/569,645

(22) Filed: Aug. 8, 2012

(65) Prior Publication Data

US 2013/0035626 A1 Feb. 7, 2013

Related U.S. Application Data

(63) Continuation of application No. PCT/JP2011/052754, filed on Feb. 9, 2011.

(30) Foreign Application Priority Data

Feb. 10, 2010 (JP) ................... 2010-028182

(51) Int. Cl.
*A61M 1/00* (2006.01)
*B01D 61/24* (2006.01)
*A61M 1/34* (2006.01)
*A61M 1/36* (2006.01)

(52) U.S. Cl.
CPC ........... *A61M 1/3643* (2013.01); *A61M 1/3437* (2014.02); *A61M 1/3431* (2014.02)
USPC ......................... 604/6.09; 210/646

(58) Field of Classification Search
CPC .................................. A61M 1/00; B01D 61/24
USPC .......................... 604/6.09; 210/646
See application file for complete search history.

(56) References Cited

U.S. PATENT DOCUMENTS

| | | | |
|---|---|---|---|
| 2002/0161322 A1* | 10/2002 | Utterberg et al. | 604/6.16 |
| 2005/0040110 A1* | 2/2005 | Felding | 210/646 |
| 2009/0312686 A1 | 12/2009 | Sakamoto et al. | |

FOREIGN PATENT DOCUMENTS

| | | |
|---|---|---|
| JP | 2001-112863 | 4/2001 |
| JP | 2004-313522 | 11/2004 |
| JP | 2007-167108 | 7/2007 |
| JP | 2009-153640 | 7/2009 |
| JP | 2009-297339 | 12/2009 |
| WO | 2007/072772 | 6/2007 |
| WO | 2009/153955 | 12/2009 |

\* cited by examiner

*Primary Examiner* — Leslie Deak
*Assistant Examiner* — Sara Sass
(74) *Attorney, Agent, or Firm* — Harness, Dickey & Pierce, P.L.C.

(57) ABSTRACT

A blood purification apparatus, during priming, has one end of the fluid infusing line L3 connected at the same location as the connected location of the fluid infusing line L3 during the blood purification treatment process. Determining whether either a pre-fluid infusion, where replenishment fluid is supplied to an arterial air trap chamber 5, or a post-fluid infusion, where the replenishment fluid is supplied to a venous air trap chamber 6, will be performed in the blood purification treatment process. The end of an arterial blood circuit 2 and the end of a venous blood circuit 3 are connected together to communicate fluid. In addition, a blood pump 4 is driven in normal rotation or in reverse rotation direction while the replenishment fluid is supplied from the fluid infusing line L3. The replenishment fluid is discharged from an overflow line 6a.

12 Claims, 7 Drawing Sheets

BLOOD PURIFICATION APPARATUS AND PRIMING METHOD THEREOF

CROSS-REFERENCE TO RELATED APPLICATIONS

This application is a continuation of International Application No. PCT/JP2011/052754, filed Feb. 9, 2011, which claims priority to Japanese Application No. 2010-028182, filed Feb. 10, 2010. The disclosures of the above applications are incorporated herein by reference.

FIELD

The present disclosure relates to a blood purification apparatus that performs a blood purification treatment using a blood purifier connected to a blood circuit, and a method of priming.

BACKGROUND

Recently, in dialysis apparatus used as a blood purification apparatus, a technique has been suggested that performs priming, reinfusion, and fluid infusion (emergency fluid infusion) using a dialysate supplied to a dialyzer during dialysis treatment (particularly, an on-line HDF or an on-line HF). For example, Patent Document 1, Japanese Laid-Open Patent Publication No. 2004-313522 discloses a dialysis apparatus that includes a fluid infusing line that has one end connected to a collection port formed in a predetermined part of a dialysate introduction line. The other end is connected to a blood circuit (arterial blood circuit or venous blood circuit). A fluid infusing pump is disposed in the fluid infusing line. In order to perform priming, the reinfusion or the fluid infusion (the emergency fluid infusion) using the dialysis apparatus, the dialysate in a dialysate introduction line is supplied to the blood circuit (the arterial blood circuit or the venous blood circuit) by driving the fluid infusing pump.

However, in a blood purifier, hereinafter called an on-line HDF that is applied to the blood dialysis filtration (HDF) and uses the dialysate as the fluid infusion, there is a need to perform the fluid infusion, including a pre-fluid infusion performing fluid infusion by the arterial blood circuit and a post-fluid infusion performing fluid infusion by the venous blood circuit, of the dialysate to the patient's blood by the ultrafiltration corresponding to a filtration treatment as the HDF treatment. An apparatus applied to the on-line HDF, is disclosed in Japanese Laid-open Patent Publication No. 2001-112863. Here, a dialysis apparatus has been suggested that has a dialyzer, a blood circuit, a dialysate introduction line, a dialysate discharging line and a fluid infusing line. The blood circuit includes an arterial blood circuit and a venous blood circuit with a blood pump. The dialysate introduction line introduces the dialysate into the dialyzer. The dialysate discharging line discharges the dialysate from the dialyzer. The fluid infusing line (a pre-fluid infusing line or a post-fluid infusing line) supplies the dialysate, of the dialysate introduction line, to the blood circuit to perform the fluid infusion without going through the dialyzer.

SUMMARY

However, in the blood purification apparatus of the related art mentioned above, the connection part of the fluid infusing line differs between priming and the blood purification treatment process. After priming is finished, a case of requiring the operation of connecting the fluid infusing line again is assumed. In that case, there is a problem in that operability is degraded when changing from priming to the blood purification treatment process. However, such a problem is similarly generated in the case of where an off-line HDF (for example, the proximal end of the fluid supplement line is connected to an accommodating device that accommodates a replenishment fluid or the like) without being limited to the case is applied to the on-line HDF as mentioned above.

The present disclosure has been made under such circumstances. A blood purification apparatus is provided that is able to transition from priming to a blood purification treatment process while maintaining the connection state of the fluid infusing line. The blood purification apparatus is able to improve operability when changing between priming and a blood purification treatment. A priming method is also provided.

According to the disclosure, a blood purification apparatus comprises a blood purifier with a blood purification membrane to perform blood purification in the blood purification membrane. An arterial blood circuit has a proximal end connected to the blood purifier. A blood pump is disposed in the arterial blood circuit. A venous blood circuit has a proximal end connected to the blood purifier. An arterial air trap chamber is connected to the arterial blood circuit. A venous air trap chamber is connected to the venous blood circuit. An overflow line extends from the top of the venous air trap chamber and can discharge liquid in the venous air trap chamber to the outside, causing the liquid to overflow. A dialysate introduction line introduces a dialysate into the blood purifier. A dialysate discharge line discharges the dialysate from the blood purifier. A fluid infusing line causes a replenishment fluid to flow in from one end. The other end is connected to the arterial air trap chamber or the venous air trap chamber. A fluid supplying device supplies the replenishment fluid, that flows in the fluid infusing line, to the arterial blood circuit or the venous blood circuit, via the arterial air trap chamber or the venous air trap chamber. The other end of the fluid infusing line is connected to the same part as that of a blood purification treatment process during priming. A tip of the arterial blood circuit is connected to a tip of the venous blood circuit in a communication state. The blood purification apparatus further includes a control device capable of controlling discharge of the replenishment fluid from the overflow line. This occurs by driving the blood pump in normal rotation or reverse rotation direction while supplying the replenishment fluid from the fluid infusing line.

In the blood purification apparatus, one end of the fluid infusing line is connected to the dialysate introduction line. The dialysate, as the replenishment fluid, is supplied to the arterial blood circuit or the venous blood circuit.

In the blood purification apparatus, the fluid supplying device includes a fluid infusing pump disposed in the fluid infusing line.

In the blood purification apparatus, the proximal end of the fluid infusing line is connected to the arterial air trap chamber. A pre-fluid infusion is performed in the blood purification treatment process. During priming, the control device drives the blood pump in a reverse rotation direction. It also controls a drive speed of the blood pump so as to be equal to or less than a supply speed of the replenishment fluid by driving the fluid supplying device.

In the blood purification apparatus, the proximal end of the fluid infusing line is connected to the venous air trap chamber. A post-fluid infusion is performed in the blood purification treatment process. During priming, the control device drives the blood pump in a normal rotation direction. It also controls a drive speed of the blood pump so as to be equal to or less than a supply speed of the replenishment fluid using the fluid supplying device.

In the blood purification apparatus, an air bubble detection device is disposed at a tip side of the venous blood circuit. During priming, the control device sequentially performs a first circulation process, driving the blood pump in reverse rotation at a predetermined speed, and a second circulation process, driving the blood pump at a speed lower than the predetermined speed. As a condition in the first circulation process, the air bubble detection device detects the presences of air bubbles.

A priming method of a blood purification apparatus includes a blood purifier with a blood purification membrane that performs blood purification in the blood purification membrane. An arterial blood circuit has a proximal end connected to the blood purifier. A blood pump is disposed in the arterial blood circuit. A venous blood circuit has a proximal end connected to the blood purifier. An arterial air trap chamber is connected to the arterial blood circuit. A venous air trap chamber is connected to the venous blood circuit. An overflow line extends from the top of the venous air trap chamber to discharge liquid in the venous air trap chamber to the outside, by causing the liquid to overflow. A dialysate introduction line introduces a dialysate into the blood purifier. A dialysate discharge line discharges the dialysate from the blood purifier. A fluid infusing line causes a replenishment fluid to flow in from one end. The other end is connected to the arterial air trap chamber or the venous air trap chamber. A fluid supplying device supplies the replenishment fluid, flowing in the fluid infusing line, to the arterial blood circuit or the venous blood circuit, via the arterial air trap chamber or the venous air trap chamber. The other end of the fluid infusing line is connected to the same site as that of a blood purification treatment process during priming. A tip of the arterial blood circuit is connected to a tip of the venous blood circuit in a communication state. The replenishment fluid is discharged from the overflow line by driving the blood pump in normal rotation or reverse rotation direction while supplying the replenishment fluid from the fluid infusing line.

The priming method of the blood purification apparatus includes one end of the fluid infusing line connected to the dialysate introduction line. The dialysate, as the replenishment fluid, is supplied to the arterial blood circuit or the venous blood circuit.

The priming method of the blood purification apparatus includes the fluid supplying device, with a fluid infusing pump, disposed in the fluid infusing line.

The priming method of the blood purification apparatus includes the proximal end of the fluid infusing line connected to the arterial air trap chamber. A pre-fluid infusion is performed in the blood purification treatment process. During priming, the blood pump is driven in a reverse rotation direction and a drive speed of the blood pump is set to be equal to or less than a supply speed of the replenishment fluid using the fluid supplying device.

The priming method of the blood purification apparatus includes the proximal end of the fluid infusing line connected to the venous air trap chamber. A post-fluid infusion is performed in the blood purification treatment process. During priming, the blood pump is driven in a normal rotation direction and a drive speed of the blood pump is set to be equal to or less than a supply speed of the replenishment fluid using the fluid supplying device.

The priming method of the blood purification apparatus includes an air bubble detection device disposed at a tip side of the venous blood circuit. During priming, the control device sequentially performs a first circulation process, driving the blood pump in reverse rotation at a predetermined speed, and a second circulation process, driving the blood pump at a speed lower than the predetermined speed. As a condition of the first circulation process, the air bubble detection device detects air bubbles.

According to the present disclosure, during priming, the other end of the fluid infusing line is connected to the same site as that of the blood purification treatment process. The arterial blood circuit is connected to the tip of the venous blood circuit in the communication state. The replenishment fluid is discharged from the overflow line by driving the blood pump in a normal rotation or reverse rotation direction while supplying the replenishment fluid from the fluid infusing line. Thus, the operation can be shifted from priming to blood purification treatment while maintaining the connection state of the fluid infusing line. Thus, it is possible to improve operability when shifting from priming to a blood purification treatment.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Hereinafter, an embodiment of the present disclosure will be specifically described with reference to the drawings.

Figure 1:
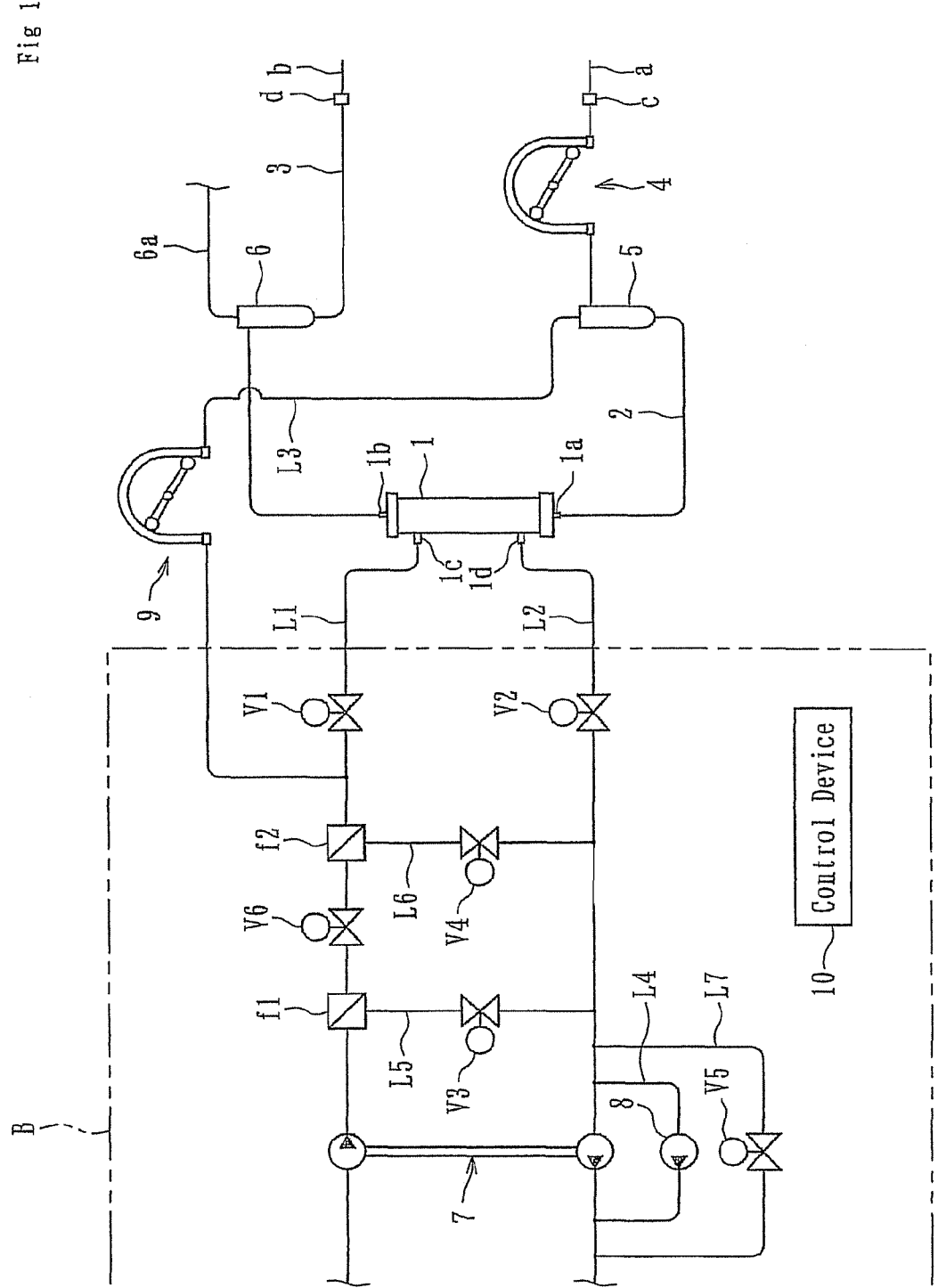
FIG. 1 is a schematic diagram of a dialysis apparatus according to a first embodiment.

A blood purification apparatus according to the present embodiment is applied to a blood dialysis apparatus that performs a pre-fluid infusion that supplies a dialysate, as a replenishment fluid, to an arterial blood circuit 2 in the blood purification treatment process. As shown in FIG. 1, the blood purification apparatus mainly includes a blood circuit and a dialysis apparatus main body B. The blood circuit includes the arterial blood circuit 2 and a venous blood circuit 3 connected to a dialyzer 1, as a blood purifier. The dialysis apparatus main body B has a dialysate introduction line L1, a dialysate discharging line L2, a fluid infusing line L3, a fluid infusing pump 9 as a fluid supplying device, and a control device 10.

The dialyzer 1 includes a blood purification membrane (not shown). Although the membrane is a hollow fiber type blood dialysis filtration membrane in the present embodiment, the membrane may include a flat membrane type, blood dialysis membrane, and a blood filtration membrane. The dialyzer 1 includes a blood introduction port 1a to introduce the blood. A blood discharge port 1b discharges the introduced blood. A dialysate introduction port 1c introduces the dialysate into the dialyzer. A dialysate discharge port 1d discharges the introduced dialysate. The blood is purified by bringing the dialysate into contact with the blood introduced from the blood introduction portion 1a via a hollow fiber. Furthermore, the dialyzer 1 is mounted so that the blood introduction port 1a faces downward.

The arterial blood circuit 2 includes a flexible tube. One end of the tube is connected to a blood introduction portion 1a of the dialyzer 1 to guide the blood collected from a patient's blood vessel into the hollow fiber of the dialyzer 1. The other end of the arterial blood circuit 2 has a connector (c) capable of attaching an arterial puncture needle (a). An arterial air trap chamber 5 is connected to the middle of the arterial blood circuit. A blood pump 4 is disposed on the tube. The arterial air trap chamber 5 is mounted in the same direction during priming and when performing the dialysis treatment. Thus, it is possible to eliminate the work of inverting the arterial air trap chamber 5 before the dialysis treatment is started. The blood pump 4 is a peristaltic type pump. It has a configuration that squeezes the flexible tube during normal rotation to cause the blood from the arterial puncture needle (a) to flow in a direction of the blood introduction port 1a of the dialyzer 1.

The venous blood circuit 3 includes a flexible tube like the arterial blood circuit 2. One end of the tube is connected to a blood introduction port 1b of the dialyzer 1 to introduce the blood passing through the hollow fiber. The other end of the venous blood circuit 3 has a connector (d) capable of attaching a venous puncture needle (b). A venous air trap chamber 6 is connected to the middle of the venous blood circuit. The venous air trap chamber 6 is mounted in the same direction during priming and when performing the dialysis treatment. Thus, it is possible to eliminate a task of inverting the venous air trap chamber 6 before the dialysis treatment is started. An overflow line 6a extends from the top of the venous air trap chamber 6. The overflow line is capable of discharging liquid in the venous air trap chamber by causing the liquid to overflow. The patient's blood collected by the arterial puncture needle (a) reaches the dialyzer 1 via the arterial blood circuit 2. It flows through the venous blood circuit 3 after the blood purification is performed. The blood returns back into the body of the patient via the venous puncture needle (b). Thus, the extracorporeal circulation is performed.

The dialysate introduction line L1 and the dialysate discharge line L2 are connected to the dialysate introduction port 1c and the dialysate discharge port 1d of the dialyzer 1, respectively. The dialysate introduced to the dialyzer 1, via the dialysate introduction line L1, can be discharged from the dialysate discharge line L2 through the outside of the hollow fiber membrane. An electromagnetic valve V1 and an electromagnetic valve V2 are connected in the middle of the dialysate introduction line L1 and the dialysate discharge line L2, respectively.

A duplex pump 7 supplies the dialyzer 1 with the dialysate, prepared to a predetermined concentration, and discharges the dialysate from the dialyzer 1. The pump 7 is connected to the dialysate introduction line L1 and the dialysate discharge line L2. Bypass lines L5 and L6 enable the dialysate introduction line L1 and the dialysate discharge line L2 to communicate with each other. The bypass lines L5 and L6 are disposed in the dialysis apparatus main body B. Electromagnetic valves V3 and V4 are disposed in the middle of the bypass lines L5 and L6, respectively. Reference numerals f1 and f2 indicate filtration filters disposed in the dialysate introduction line L1. An electromagnetic valve V6 is disposed between the filtration filters f1 and f2.

The dialysate discharge line L2 is formed with bypass lines L4 and L7 that bypass the duplex pump 7. An ultrafiltration pump 8, for removing the water content from the patient's blood flowing in the dialyzer 1, is disposed in the bypass line L4. Electromagnetic valve V5, capable of opening or closing the flow route, is disposed in the bypass line L7.

One end of the fluid infusing line L3 is connected to a collection port (not shown) formed in a predetermined location of the dialysate introduction line L1. The dialysate (replenishment fluid) can flow from one end. The other end provides a flow route (for example, a flexible tube or the like) connected to the top of the arterial air trap chamber 5. The collection port is formed in the dialysis apparatus main body B. The dialysate introduction line L1 and the arterial air trap chamber 5 can communicate with each other, by connecting one end of the fluid infusing line L3 to the collection port.

The fluid infusing pump 9, acting as the fluid supplying device, is disposed in the fluid infusing line L3. The fluid infusing pump 9 supplies the dialysate (replenishment fluid) flowing in the fluid infusing line L3 to the arterial blood circuit 2 via the arterial air trap chamber 5. As a result, one end and the other end of the fluid infusing line L3 are connected to the dialysate introduction line L1 and the arterial air trap chamber 5, respectively. Thus, by driving (normal rotation) the fluid infusing pump 9 it is possible to perform the pre-fluid infusion, a fluid infusion that supplies the dialysate as the replenishment fluid to the arterial blood circuit 2 in the blood purification treatment process. Like the blood pump 4, the fluid infusing pump 9 is a peristaltic type pump. It has a configuration that can squeeze the tube constituting the fluid infusing line L3, when being driven, to cause the dialysate to flow.

The fluid infusing line L3 is disposed with a clamp device (not shown) that is capable of opening and closing the flow route. After the fluid infusing line L3 is connected to the collection port by a worker, the clamp device is in the closed state until the dialysate is circulated and the flow route is closed. Moreover, if necessary (during priming, reinfusion, fluid infusion or the like), the clamp device is in the open state by a worker, the dialysate introduction line L1 communicates with the blood circuit (arterial blood circuit 2).

The control device 10 is formed from, for example, a microcomputer or the like that can control the opening and the closing of various electromagnetic valves V1 to V6, disposed in the dialysis apparatus, and an actuator of the blood pump 4, the fluid infusing pump 9 or the like. Particularly, in the present embodiment, it is possible to perform the control so as to drive the blood pump 4 in a reverse rotation direction while supplying the dialysate (replenishment fluid) from the fluid infusing line L3 and discharge the dialysate (replenishment fluid) from the overflow line 6a by driving the fluid infusing pump 9 during priming.

Figure 2:
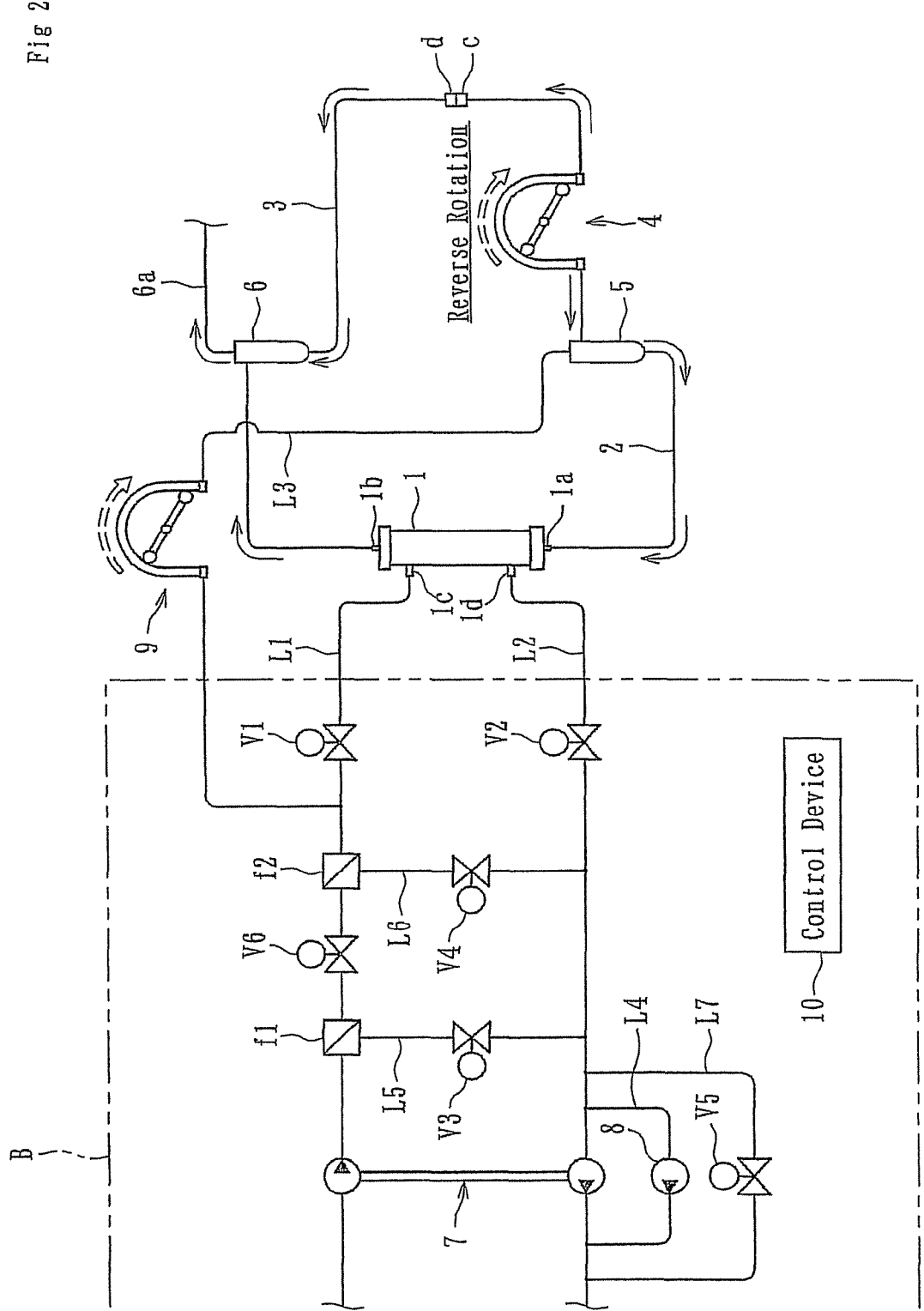
FIG. 2 is a schematic diagram of a state performing priming (air purging) in the dialysis apparatus.

More specifically, during priming particularly, during an air purging process in the blood circuit and in the blood flow route of the dialyzer 1, as shown in FIG. 2, the other end of the fluid infusing line L3 is connected to the same site. The pre-fluid infusion and the blood purification treatment process, in the present embodiment, are performed at the top of the arterial air trap chamber 5. The connection site of the fluid infusing line L3 is determined depending on whether any one of the pre-fluid infusion, supplying the dialysate (replenishment fluid) to the arterial air trap chamber 5, and the post-fluid infusion, supplying the dialysate (replenishment fluid) to the venous air trap chamber 6, is performed in the blood purification treatment process. The tip (connector c) of the arterial blood circuit 2 is connected to the tip (connector d) of the venous blood circuit 3 in the communication state.

In such a state, the blood pump 4 is driven in a reverse rotation direction while supplying the dialysate (replenishment fluid) from the fluid infusing line L3, by driving the fluid infusing pump 9, using the control device 10. The dialysate (replenishment fluid) is discharged from the overflow line 6a. At this time, the blood pump 4 is driven in a reverse rotation direction by the control device 10. The drive speed (flow speed) of the blood pump 4 is controlled so as to be equal to or less than the supply speed (flow speed) of the dialysate (replenishment fluid) by driving the fluid infusing pump 9 (fluid supplying device).

Furthermore, a part of the dialysate (replenishment fluid) supplied to the arterial air trap chamber 5, by the fluid infusing line L3, is divided into the flow toward the connection section (the connection sections of the connectors c and d) between the tip of the arterial blood circuit 2 and the tip of the venous blood circuit 3 and the flow toward the dialyzer 1. The respective flows are joined to each other in the venous air trap chamber 6. The flows are discharged from the overflow line 6a to the outside. In the process of the flow of the dialysate (replenishment fluid), air in the blood circuit and the blood flow route of the dialyzer 1 is discharged to the outside via the overflow line 6a.

According to the present embodiment, during priming, the other end of the fluid infusing line L3 is connected to the same site as the connection site of the fluid infusing line L3. It is determined depending on whether any one of the pre-fluid infusion, supplying the dialysate (replenishment fluid) to the arterial air trap chamber 5, and the post-fluid infusion, supplying the dialysate (replenishment fluid) to the venous air trap chamber 6, is performed in the blood purification treatment process. The tip of the arterial blood circuit 2 is connected to the tip of the venous blood circuit 3 in the communication state. Furthermore, the blood pump 4 is driven in a reverse rotation direction while supplying the dialysate (replenishment fluid) from the fluid infusing line L3. The dialysate (replenishment fluid) is discharged from the overflow line 6a. Thus, the operation can be shifted from priming to blood purification treatment while maintaining the connection state of the fluid infusing line L3. Thus, it is possible to improve operability when shifting from priming to blood purification treatment.

According to the present embodiment, the control device 10 drives the blood pump 4 in a reverse rotation direction and controls the drive speed (flow speed) of the blood pump 4 so that it is equal to or less than the supply speed (flow speed) of the dialysate (replenishment fluid) using the fluid infusing pump 9 (fluid supplying device). Thus, priming can be performed by causing the dialysate (replenishment fluid) to flow in any of the arterial blood circuit 2 and the venous blood circuit 3. More reliable and smoother priming (air purging) can be performed.

Figure 3:
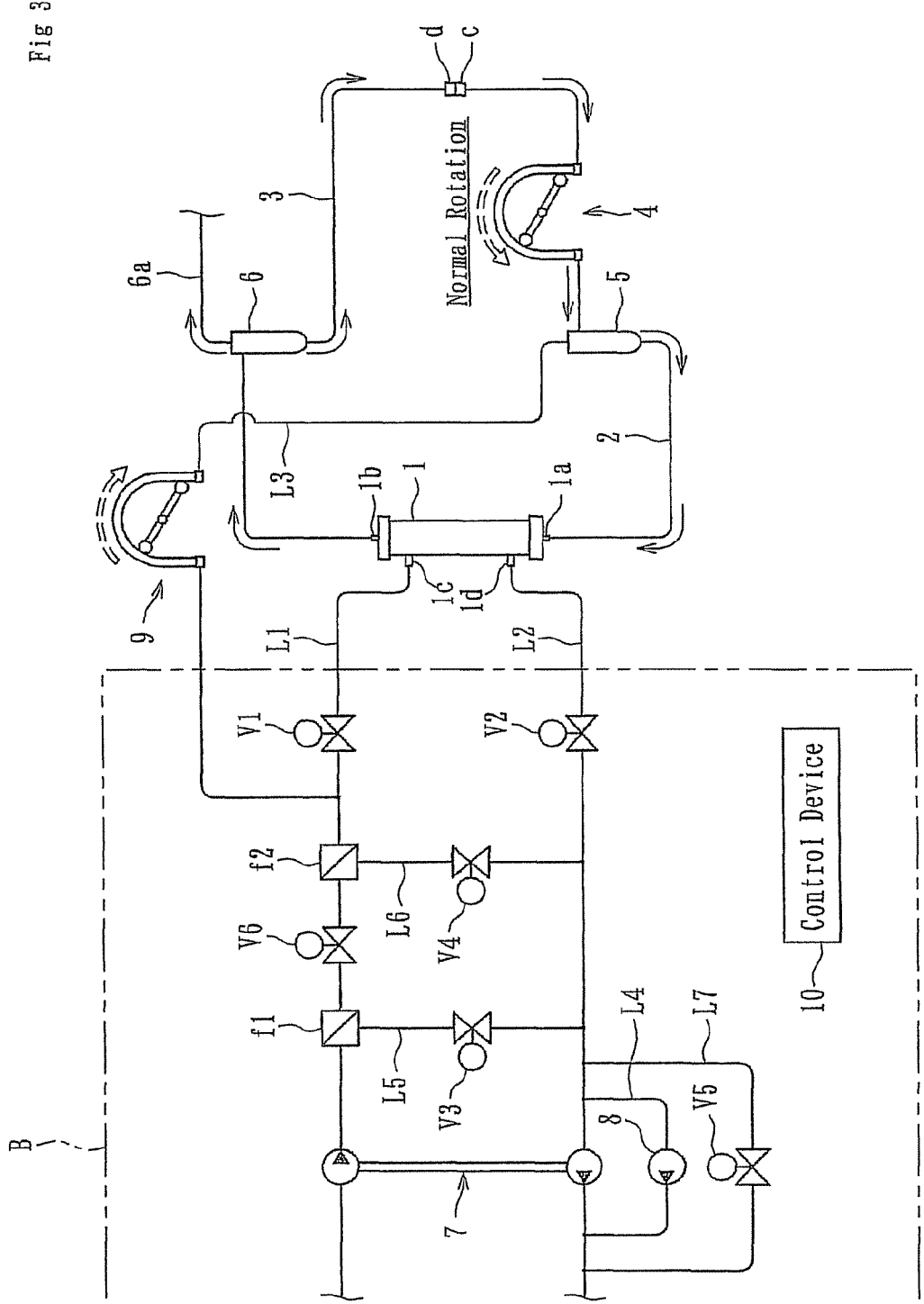
FIG. 3 is a schematic diagram of a state performing priming (cleaning) in the dialysis apparatus.

In the present embodiment, air purging is deemed finished after a predetermined time elapses or an amount of rotation of the blood pump 4 or the fluid infusing pump 9, as shown in FIG. 3. The control device 10 controls drive of the blood pump 4 in a normal rotation direction while maintaining the driving of the fluid infusing pump 9. As a result, the dialysate (replenishment fluid) is circulated in the blood circuit and the blood flow route of the dialyzer 1 in one direction. The dialysate (replenishment fluid) can be discharged from the overflow line 6a to the outside. The cleaning process can be performed after air purging in the priming process.

Next, a second embodiment of the present disclosure will be described.

Figure 4:
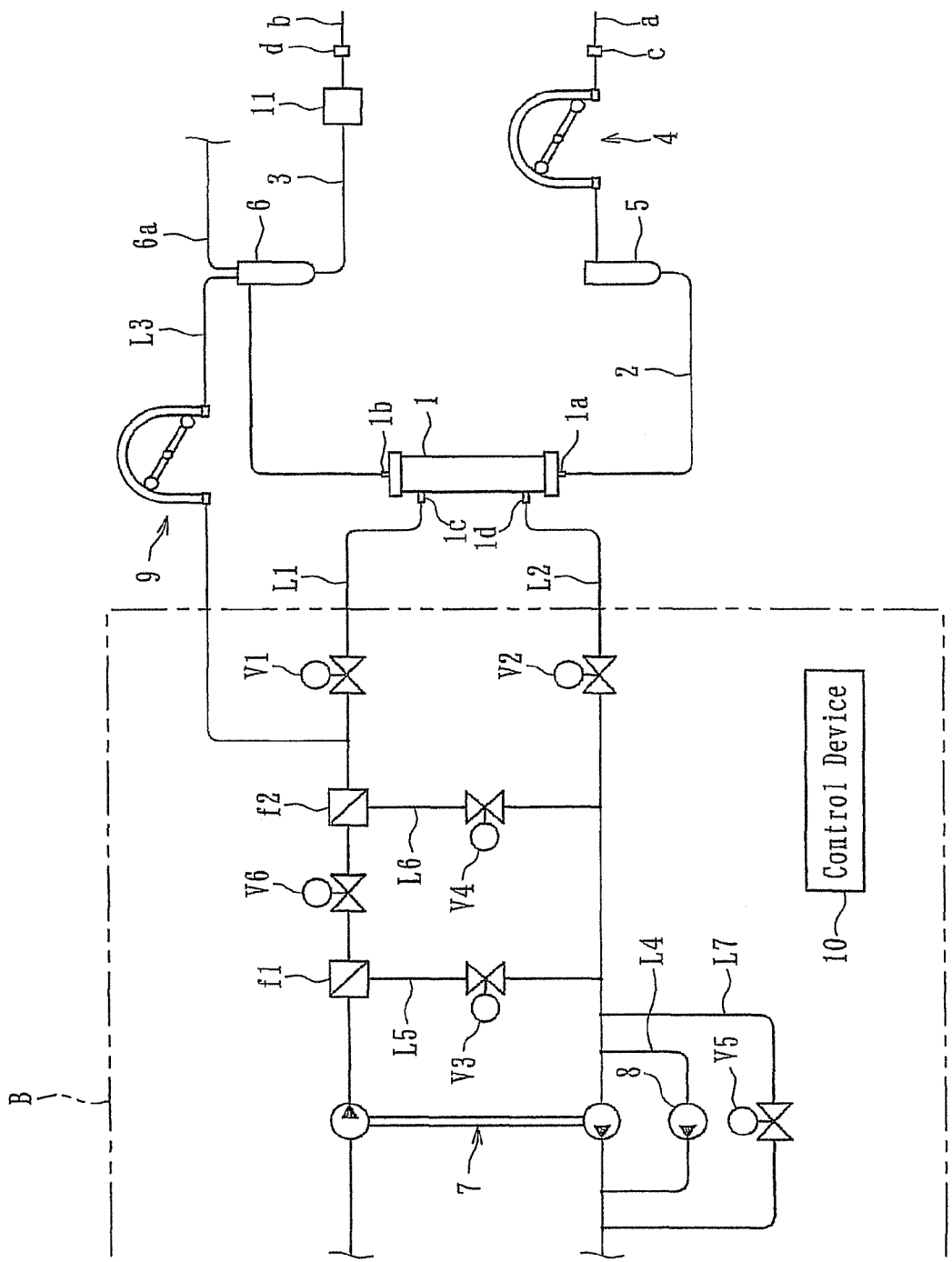
FIG. 4 is a schematic diagram of a dialysis apparatus according to a second embodiment.

A blood purification apparatus according to the present embodiment is applied to a blood dialysis apparatus that performs a post-fluid infusion that supplies the dialysate, as a replenishment fluid, to a venous blood circuit 3 in the blood purification treatment process. As shown in FIG. 4, the blood purification apparatus includes a blood circuit and a dialysis apparatus main body B. The blood circuit includes the arterial blood circuit 2 and a venous blood circuit 3 connected to a dialyzer 1, as a blood purifier. The dialysis apparatus main body B has a dialysate introduction line L1, a dialysate discharging line L2, a fluid infusing line L3, a fluid infusing pump 9 as a fluid supplying device, a control device 10, and an air bubble detection device 11.

The air bubble detection device 11 includes a sensor that is disposed on the tip side (near the connector d) of the venous blood circuit 3 to detect air bubbles in the venous blood circuit 3. The air bubble detection device 11 detects the presence or the absence of air bubbles in the blood circulating extracorporeally. As a result, in the blood purification treatment process, when air bubbles are detected by the air bubble detection device 11, the extracorporeal circulation is stopped and stability can be improved.

One end of the fluid infusing line L3 is connected to a collection port (not shown) formed at a predetermined location of the dialysate introduction line L1. The dialysate (replenishment fluid) can flow in from the one end. The other end defines a flow route (for example, a flexible tube or the like) connected to the top of the venous air trap chamber 6. The collection port is constituted by a port formed in the dialysis apparatus main body B. The dialysate introduction line L1 and the venous air trap chamber 6 can communicate with each other by connecting one end of the fluid infusing line L3 to the collection port.

The fluid infusing pump 9, as the fluid supplying device, is disposed in the fluid infusing line L3. The fluid infusing pump 9 supplies the dialysate (replenishment fluid) flowing in the fluid infusing line L3 to the venous blood circuit 3, via the venous air trap chamber 6. As a result, one end and the other end of the fluid infusing line L3 are connected to the dialysate introduction line L1 and the venous air trap chamber 6, respectively. Thus, by driving (normal rotation) the fluid infusing pump 9, it is possible to perform the post-fluid infusion, supplying the dialysate as the replenishment fluid to the venous blood circuit 3, in the blood purification treatment process. Furthermore, as in the first embodiment, the fluid infusing pump 9 is a peristaltic type pump. The pump 9 has a configuration that can squeeze the tube constituting the fluid infusing line L3 when being driven to cause the dialysate to flow.

The fluid infusing line L3 includes a clamp device (not shown) capable of opening and closing the flow route, similar to the first embodiment. After the fluid infusing line L3 is connected to the collection port by a worker, the clamp device is in the closed state until the dialysate is circulated and the flow route is closed. Moreover, if necessary during priming, reinfusion, fluid infusion or the like, and the clamp device is in an open state by a worker, the dialysate introduction line L1 communicates with the blood circuit, venous blood circuit 3.

As in the first embodiment, the control device 10 is formed by, for example, a microcomputer or the like that can control the opening and the closing of various electromagnetic valves V1 to V6 disposed in the dialysis apparatus, and an actuator of the blood pump 4, the fluid infusing pump 9 or the like. Particularly, in the present embodiment, it is possible to control drive of the blood pump 4 in a normal rotation direction while supplying the dialysate (replenishment fluid) from the fluid infusing line L3 and discharge the dialysate (replenishment fluid) into the overflow line 6a, during priming, by driving the fluid infusing pump 9.

Figure 5:
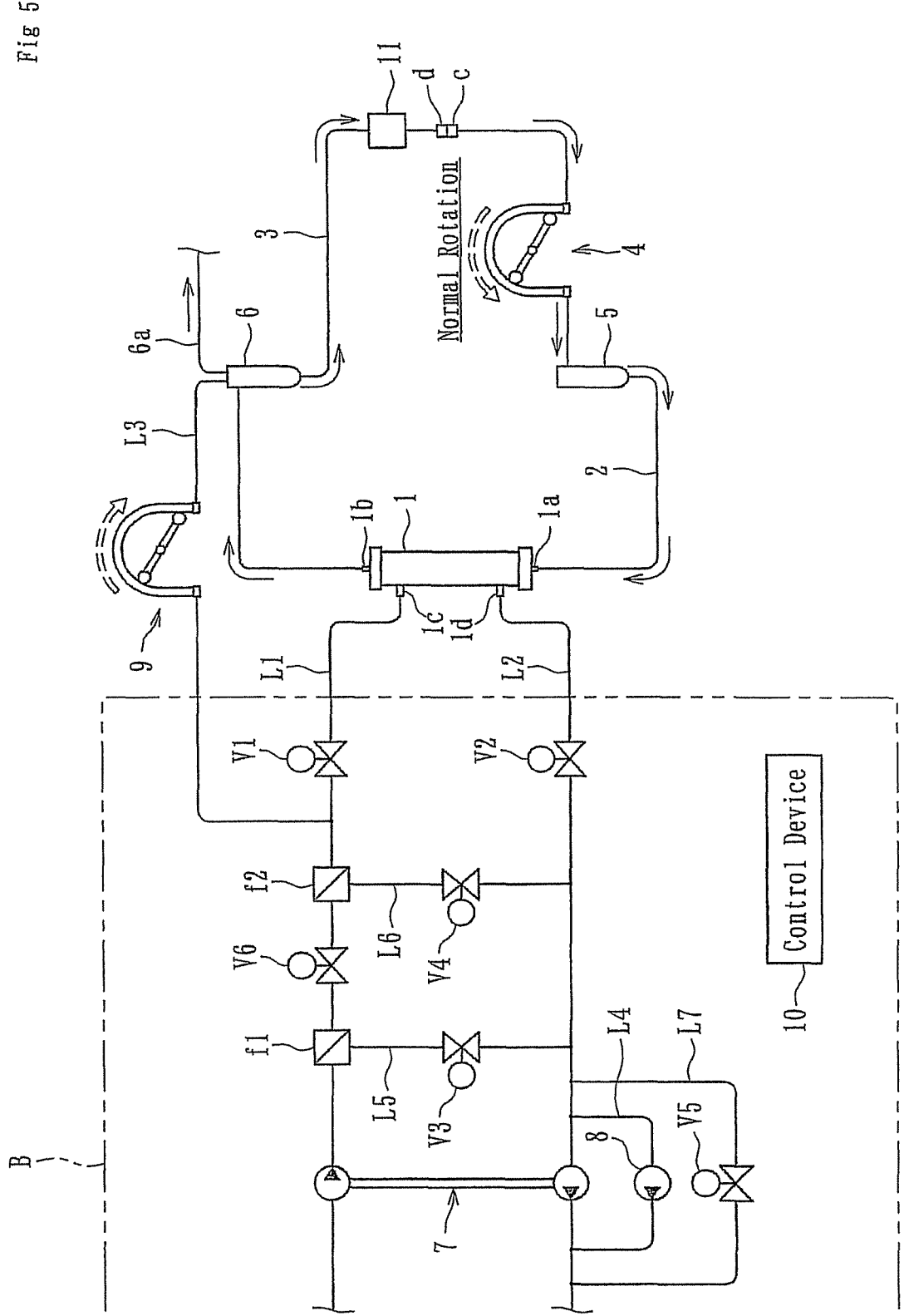
FIG. 5 is a schematic diagram of a state performing priming (air purging) in the dialysis apparatus.

During priming, particularly during an air purging process in the blood circuit and in the blood flow route of the dialyzer 1 as shown in FIG. 5, the other end of the fluid infusing line L3 is connected to the same site. The post-fluid infusion is performed in the blood purification treatment process in the present embodiment at the top of the venous air trap chamber 6. The connection site of the fluid infusing line L3 is determined depending on whether any one of the pre-fluid infusion, supplying the dialysate (replenishment fluid) to the arterial air trap chamber 5, and the post-fluid infusion, supplying the dialysate (replenishment fluid) to the venous air trap chamber 6, is performed in the blood purification treatment process. The tip (connector c) of the arterial blood circuit 2 is connected to the tip (connector d) of the venous blood circuit 3 in the communication state.

In such a state, the control device 10 controls the blood pump 4 to drive it in a normal rotation direction while supplying the dialysate (replenishment fluid) from the fluid infusing line L3 by driving the fluid infusing pump 9. The dialysate (replenishment fluid) is discharged from the overflow line 6a. At this time, the blood pump 4 is driven in a normal rotation direction by the control device 10. The drive speed (flow speed) of the blood pump 4 is controlled so as to be equal to or less than the supply speed (flow speed) of the dialysate (replenishment fluid) by driving the fluid infusing pump 9 (fluid supplying device). Furthermore, by driving only the fluid infusing pump 9 in advance to inject the dialysate (replenishment fluid) into the venous air trap chamber 6, air to be sent to the dialyzer 1 can be reduced. Thus, more efficient priming is possible.

A part of the dialysate (replenishment fluid) supplied to the venous air trap chamber 6 by the fluid infusing line L3 becomes the flow toward the connection section (the connection sections of the connectors c and d) between the tip of the arterial blood circuit 2 and the tip of the venous blood circuit 3. The other part becomes the flow discharged from the overflow line 6a. However, in a case where the drive speed (flow speed) of the blood pump 4 is equal to the supply speed (flow speed) of the dialysate (replenishment fluid), by driving the fluid infusing pump 9 (fluid supplying device), the other part can also become the flow toward the connection section side between the tip of the arterial blood circuit 2 and the tip of the venous blood circuit 3. In the process of the flow of the dialysate (replenishment fluid), air in the blood circuit and the blood flow route of the dialyzer 1 is discharged to the outside via the overflow line 6a.

Figure 6:
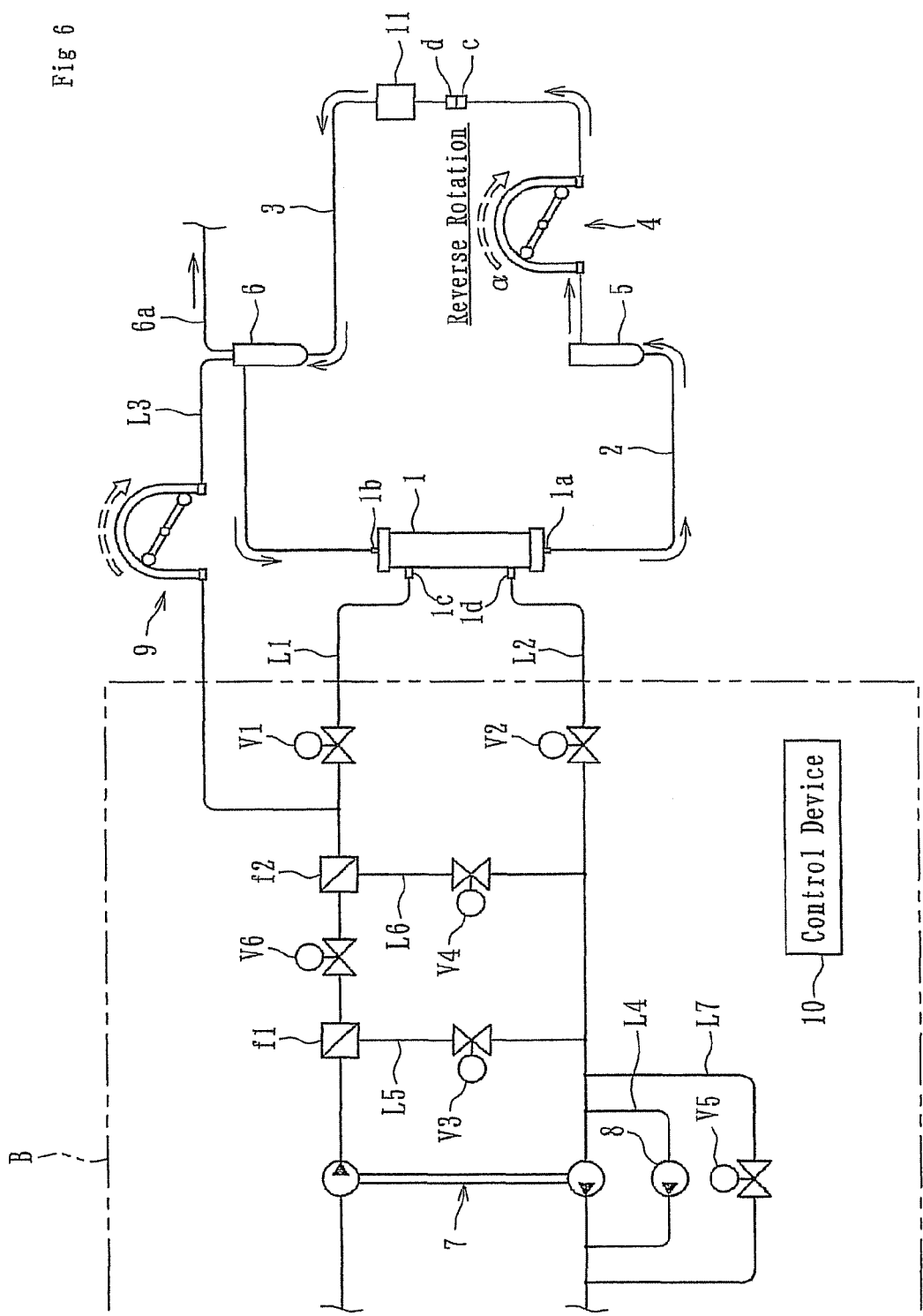
FIG. 6 is a schematic diagram of a state when performing priming (a first circulation process) in the dialysis apparatus.
Figure 7:
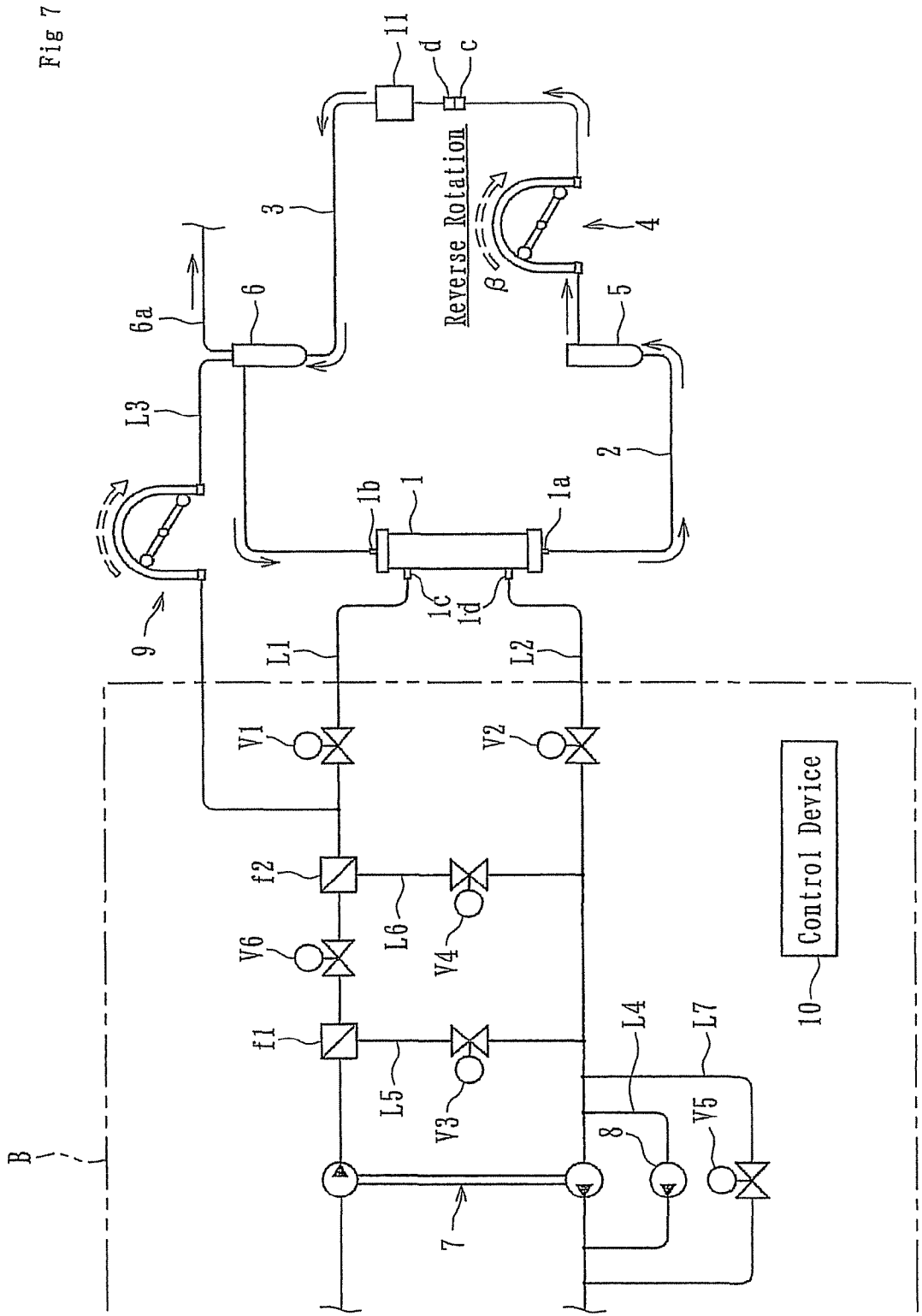
FIG. 7 is a schematic diagram of a state when performing priming (a second circulation process) in the dialysis apparatus.

After performing the process as mentioned above, the control device 10 performs a first circulation process by driving the blood pump 4 in a reverse rotation direction at a high speed (for example, a flow speed α) as shown in FIG. 6. It also performs a second circulation process by driving the blood pump 4 in a reverse rotation direction at low speeds (for example, a flow speed β slower than the flow speed α). The air bubble detection device 11 detects the air bubbles in the condition of the first circulation process, as shown in FIG. 7. As a result, it is possible to reliably capture the air bubbles trapped in the arterial air trap chamber 5 by the venous air trap chamber 6 and discharge the air bubbles to the outside via the overflow line 6a. Thus, it is possible to reliably prevent the air bubbles from reaching the dialyzer 1. Furthermore, priming can be completed at an early stage. Herein, by always driving the blood pump 4 in a reverse rotation direction at the flow speed α to perform priming, the air bubble detection device 11 can be eliminated. However, in that case, since it is required for a long time, it is preferable to perform the air bubble detection using the air bubble detection device 11 as mentioned above.

In the first circulation process and the second circulation process according to the present embodiment, the fluid infusing pump 9 may be driven or may be stopped. The flow speeds α and β can be set to an arbitrary drive speed regardless of the driving speed of the fluid infusion speed. Moreover, in a condition where the air bubbles are not detected for a predetermined time by the air bubble detection device 11, priming (air purging) is finished. Furthermore, after performing air purging, as in the first embodiment (see FIG. 3), the control device 10 controls driving of the blood pump 4 in normal rotation direction while maintaining the driving of the fluid infusing pump 9. As a result, the dialysate (replenishment fluid) is circulated in one direction in the blood circuit and the blood flow route of the dialyzer 1. The dialysate (replenishment fluid) can be discharged from the overflow line 6a to the outside. Thus, the cleaning process can be performed after air purging in the priming process.

According to the present embodiment, during priming, the other end of the fluid infusing line L3 is connected to the same site as the connection site of the fluid infusing line L3. Thus, it is determined whether any one of the pre-fluid infusion, supplying the dialysate (replenishment fluid) to the arterial air trap chamber 5, or the post-fluid infusion, supplying the dialysate (replenishment fluid) to the venous air trap chamber 6, is performed in the blood purification treatment process. The tip of the arterial blood circuit 2 is connected to the tip of the venous blood circuit 3 in the communication state. Furthermore, the blood pump 4 is driven in a reverse rotation direction while supplying the dialysate (replenishment fluid) from the fluid infusing line L3. The dialysate (replenishment fluid) is discharged from the overflow line 6a. Thus, the operation can be shifted from priming to blood purification treatment while maintaining the connection state of the fluid infusing line L3. Thus, it is possible to improve operability when shifting from priming to blood purification treatment.

Furthermore, according to the present embodiment, the control device 10 drives the blood pump 4 in a normal rotation direction and controls the drive speed (flow speed) of the blood pump 4 so as to be equal to or less than the supply speed (flow speed) of the dialysate (replenishment fluid), by driving the fluid infusing pump 9 (fluid supplying device). Thus, priming can be performed by causing the dialysate (replenishment fluid) to flow in any of the arterial blood circuit 2 and the venous blood circuit 3. Thus, a more reliable and smoother priming (air purging) can be performed.

The control device 10 sequentially performs the first circulation process, driving the blood pump 4 in reverse rotation direction at a high speed, and the second circulation process, driving the blood pump 4 in a reverse rotation direction at low speeds. Thus, the air bubble detection device 11 detects air bubbles in the first circulation process. Accordingly, it is possible to smoothly perform the premature termination of priming and the removal of air bubbles in the arterial air trap chamber 5. Thus, since there is no need to invert the arterial air trap chamber 5, it is possible to further improve operability during priming and shifting from priming to blood purification treatment.

Although the embodiments have been described as above, the present disclosure is not limited. The present disclosure is not limited to, for example, the application of the on-line HDF, but may be applied to the off-line HDF. For example, the proximal end of the fluid infusing line connects to the accommodating device to accommodate the replenishment fluid (a so-called fluid infusion which is not limited to the dialysate or the like). Furthermore, in the present embodiments, although the fluid infusing pump 9, as the fluid supplying device, is disposed in the fluid infusing line L3, for example, another pump (a duplex pump 7, a cascade pump or the like in the present embodiment) may be used as the fluid supplying device. Furthermore, in the second embodiment, although the air bubble detection device 11 is disposed at the tip side of the venous blood circuit 3, the air bubble detection device may be eliminated. Alternately, in the first embodiment, the air bubble detection device 11 may be disposed at the tip side of the venous blood circuit 3.

A blood purification apparatus includes a priming method. During priming, the other end of the fluid infusing line is connected to the same site as the connection site of the fluid infusing line. It is determined whether any one of the pre-fluid infusion, supplying the replenishment fluid to the arterial air trap chamber, or the post-fluid infusion, supplying the replenishment fluid to the venous air trap chamber, is performed in the blood purification treatment process. The tip of the arterial blood circuit is connected to the tip of the venous blood circuit in the communication state. The blood pump is driven in a reverse rotation direction while supplying the replenishment fluid from the fluid infusing line. The replenishment fluid is discharged from the overflow line. The disclosed apparatus can be applied to an apparatus with other added functions.

The present disclosure has been described with reference to a preferred embodiment. Obviously, modifications and alternations will occur to those of ordinary skill in the art upon reading and understanding the preceding detailed description. It is intended that the present disclosure be construed to include all such alternations and modifications insofar as they come within the scope of the appended claims or their equivalents.

What is claimed is:

1. A blood purification apparatus comprising:
    a blood purifier including a blood purification membrane performing blood purification in the blood purification membrane;
    an arterial blood circuit with a proximal end connected to the blood purifier and a blood pump disposed in the arterial blood circuit;
    a venous blood circuit with a proximal end connected to the blood purifier;
    an arterial air trap chamber connected to the arterial blood circuit;
    a venous air trap chamber connected to the venous blood circuit;
    an overflow line extending from a top of the venous air trap chamber for discharging replenishment fluid in the venous air trap chamber to the ambient conditions by causing the replenishment fluid to overflow;
    a dialysate introduction line introducing a dialysate into the blood purifier;
    a dialysate discharge line discharging the dialysate from the blood purifier;
    a fluid infusing line enabling a replenishment fluid to flow in from one end, and another end connected directly to the arterial air trap chamber or directly to the venous air trap chamber;
    a fluid supplying device supplying the replenishment fluid flowing in the fluid infusing line to the arterial blood circuit or the venous blood circuit via the arterial air trap chamber or the venous air trap chamber; and
    during priming, the other end of the fluid infusing line is connected to the same site as that of a blood purification treatment process, a tip of the arterial blood circuit is directly connected to a tip of the venous blood circuit in a communication state, and the blood purification apparatus further includes a control device capable of controlling discharge of the replenishment fluid from the overflow line, by driving the blood pump in normal rotation or reverse rotation direction while supplying the replenishment fluid from the fluid infusing line.

2. The blood purification apparatus according to claim 1, wherein one end of the fluid infusing line is connected to the dialysate introduction line and the dialysate as the replenishment fluid is supplied to the arterial blood circuit or the venous blood circuit.

3. The blood purification apparatus according to claim 1, wherein the fluid supplying device includes a fluid infusing pump disposed in the fluid infusing line.

4. The blood purification apparatus according to claim 1, wherein a proximal end of the fluid infusing line is connected to the arterial air trap chamber and a pre-fluid infusion is performed in the blood purification treatment process, and
    during priming, the control device drives the blood pump in a reverse rotation direction and controls a drive speed of the blood pump so as to be equal to or less than a supply speed of the replenishment fluid by driving the fluid supply device.

5. The blood purification apparatus according to claim 1, wherein the proximal end of the fluid infusing line is connected to the venous air trap chamber and a post-fluid infusion is performed in the blood purification treatment process, and
    during priming, the control device drives the blood pump in a normal rotation direction and controls a drive speed of the blood pump so as to be equal to or less than a supply speed of the replenishment fluid by driving the fluid supplying device.

6. The blood purification apparatus according to claim 5, wherein an air bubble detection device is disposed at a tip side of the venous blood circuit, and during priming, the control device sequentially performs a first circulation process, driving the blood pump in a reverse rotation direction at a predetermined speed, and a second circulation process, driving the blood pump at a speed lower than the predetermined speed when the air bubble detection device detects air bubbles in the first circulation process.

7. A priming method of a blood purification apparatus comprising:
    a blood purifier including a blood purification membrane and performing blood purification in the blood purification membrane;
    an arterial blood circuit including a proximal end connected to the blood purifier and a blood pump disposed in the arterial blood circuit;
    a venous blood circuit including a proximal end connected to the blood purifier;
    an arterial air trap chamber connected to the arterial blood circuit; a venous air trap chamber connected to the venous blood circuit;
    an overflow line extending from a top of the venous air trap chamber and discharging replenishment fluid in the venous air trap chamber to the ambient conditions by causing the replenishment fluid to overflow;
    a dialysate introduction line introducing a dialysate into the blood purifier;
    a dialysate discharge line discharging the dialysate from the blood purifier;
    a fluid infusing line enabling a replenishment fluid to flow in from one end, and another end connected directly to the arterial air trap chamber or directly to the venous air trap chamber;

a fluid supplying device supplying the replenishment fluid flowing in the fluid infusing line to the arterial blood circuit or the venous blood circuit via the arterial air trap chamber or the venous air trap chamber; and during priming, the other end of the fluid infusing line is connected to the same site as that of a blood purification treatment process, a tip of the arterial blood circuit is directly connected to a tip of the venous blood circuit in a communication state, and the replenishment fluid is discharged from the overflow line by driving the blood pump in a normal rotation or reverse rotation direction while supplying the replenishment fluid from the fluid infusing line.

8. The priming method of the blood purification apparatus according to claim 7, wherein one end of the fluid infusing line is connected to the dialysate introduction line, and the dialysate, as the replenishment fluid, is supplied to the arterial blood circuit or the venous blood circuit.

9. The priming method of the blood purification apparatus according to claim 7, wherein the fluid supplying device includes a fluid infusing pump disposed in the fluid infusing line.

10. The priming method of the blood purification apparatus according to claim 7, wherein a proximal end of the fluid infusing line is connected to the arterial air trap chamber and a pre-fluid infusion is performed in the blood purification treatment process, and during priming, the blood pump is driven in a reverse rotation direction and a drive speed of the blood pump is set to be equal to or less than a supply speed of the replenishment fluid by driving the fluid supplying device.

11. The priming method of the blood purification apparatus according to claim 7, wherein the proximal end of the fluid infusing line is connected to the venous air trap chamber and a post-fluid infusion is performed in the blood purification treatment process; and during priming, the blood pump is driven in a normal rotation direction and a drive speed of the blood pump is set to be equal to or less than a supply speed of the replenishment fluid by driving the fluid supplying device.

12. The priming method of the blood purification apparatus according to claim 11, wherein an air bubble detection device is disposed at a tip side of the venous blood circuit, and during priming, the control device sequentially performs a first circulation process, driving the blood pump in a reverse rotation direction at a predetermined speed, and a second circulation process, driving the blood pump at a speed lower than the predetermined speed when the air bubble detection device detects air bubbles in the first circulation process.

\* \* \* \* \*